United States Patent [19]

Furlan et al.

[11] Patent Number: 5,438,145
[45] Date of Patent: Aug. 1, 1995

[54] PROCESS FOR THE PREPARATION OF AMLODIPINE BENZENESULPHONATE

[75] Inventors: Borut Furlan, Ljubljana; Anton Čopar, Šmartno pri Litiji; Alenka Jeriha, Ljubljana-Polje, all of Slovenia

[73] Assignee: LEK, tovarna farmecevtskih in kemicnih izdelkov, Slovenia

[21] Appl. No.: 295,023

[22] Filed: Aug. 25, 1994

Related U.S. Application Data

[62] Division of Ser. No. 149,735, Nov. 10, 1993, Pat. No. 5,389,654.

[51] Int. Cl.⁶ .......................................... C07D 211/86
[52] U.S. Cl. .................................................. 546/321
[58] Field of Search ........................................ 546/321

[56] References Cited

U.S. PATENT DOCUMENTS 4,572,909 2/1986 Campbell et al. ............. 514/356
4,879,303 11/1989 Davison et al. ............... 514/356

*Primary Examiner*—Jane Fan
*Attorney, Agent, or Firm*—Pollock, Vande Sande & Priddy

[57] ABSTRACT

There is disclosed a process for the preparation of 3-ethyl 5-methyl (±) 2-[(2-aminoethoxy)methyl]-4-(2-chlorophenyl)-1,4-dihydro-6-methyl-3,5-pyridine-dicarboxylate monobenzenesulphonate (amlodipine benzenesulphonate) of formula

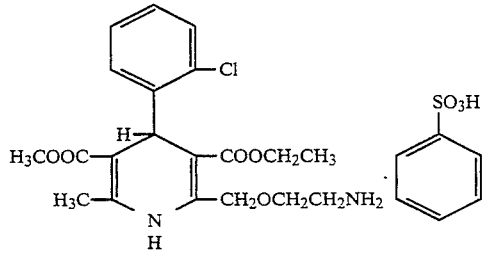

wherein 3-ethyl 5-methyl (±) 2-[2-(N-tritylamino)-ethoxymethyl]-4-(2-chlorophenyl)-1,4-dihydro-6-methyl-3,5-pyridinecarboxylate is reacted with benzenesulphonic acid in a methanolic or an aqueous methanolic medium at a temperature from 20° C. to the reflux temperature and the title compound is isolated and purified.

Amlodipine benzene sulphonate is a valuable anti-ischaemic and anti-hypertensive agent.

5 Claims, No Drawings

PROCESS FOR THE PREPARATION OF AMLODIPINE BENZENESULPHONATE

This is a divisional application of Ser. No. 08/149,735, filed on Nov. 10, 1993, now U.S. Pat. No. 5,389,654 issued Feb. 14, 1995.

TECHNICAL FIELD OF THE INVENTION

The present invention belongs to the field of chemistry of heterocyclic compounds as well as to the field of pharmaceutical industry and relates to a novel process for the preparation of amlodipine benzenesulphonate of the formula

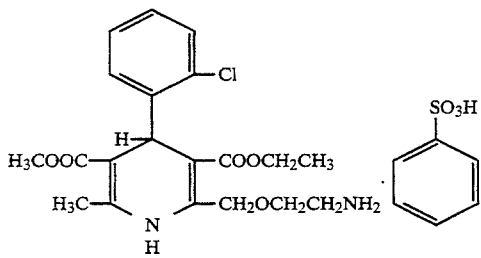

Amlodipine benzenesulphonate is a potent calcium channel blocker and it represents a valuable anti-ischaemic and anti-hypertensive agent.

TECHNICAL PROBLEM

There exists a constant need for the preparation of amlodipine benzenesulphonate in a simple and easily feasible way which would afford the desired substance in high yield and high purity, without any need for a previous preparation and isolation of amlodipine in the form of its base.

PRIOR ART

Amlodipine is the generic name for 3-ethyl 5-methyl (±) 2-[(2-aminoethoxy)methyl]-4-(2-chlorophenyl)-1,4-dihydro-6-methyl-3,5-pyridine dicarboxylate, which was disclosed in EP-B1-0 089 167 as a new substance and a useful anti-ischaemic and anti-hypertensive agent. Pharmaceutically acceptable acid addition salts of amlodipine were disclosed as well, the maleate salt being presented as the most preferred compound.

EP-B1-0 244 944 discloses a novel benzenesulphonate (besylate) salt of amlodipine and galenic forms containing the same. Because of its extraordinary solubility, high stability, non-hygroscopicity and good processability, this salt is outstanding suitable for the preparation of galenic forms of amlodipine. According to said patent, amlodipine benzenesulphonate is prepared by reacting amlodipine in its free base form with benzenesulphonic acid or ammonium benzenesulphonate in an inert solvent such as industrial methanol at the temperature of 5° C.

Amlodipine in its free base form can be prepared in different ways as explained in the above mentioned EP-B1-0 089 167. According to these processes amlodipine can be prepared by the removal of the aminoprotecting group from the precursor of amlodipine, i.e. the 1,4-dihydropyridine derivative, wherein the 2-standing amino group is protected by selected protective groups.

In case the amino group is protected by a benzyl group, the latter is removed by catalytic hydrogenation over a palladium catalyst in a solvent such as methanol at room temperature. When the protective group is a 2,2,2-trichloroethoxycarbonyl (—COOCH$_2$CCl$_3$) group, it is removed by reduction with zinc in either formic or acetic acid. In case the protective group is a phthalimido group, the phthaloyl moiety of this group is removed by reaction with a primary amine such as methylamine or hydrazine hydrate in a solvent such as ethanol, or with an alkali metal hydroxide such as potassium hydroxide, followed by the reaction with hydrochloric or sulphuric acid in a mixture of tetrahydrofuran and water at a temperature ranging from room temperature to reflux temperature. If desired, the obtained amlodipine is converted to its pharmaceutically acceptable acid addition salt.

In EP-B1-0 089 167, there is also described a process for the preparation of amlodipine from its precursor having a 2-standing azido group, which is convertible to the amino group by reduction e.g. with triphenylphosphine or zinc and hydrochloric acid or by hydrogenation over a palladium catalyst.

A disadvantage of said processes are relatively poor yields of said precursor of amlodipine, which is prepared by Hantzsch's synthesis of asymmetrical 1,4-dihydropyridine esters. The same is true for the reduction of the azido compound to amlodipine; moreover, the manipulation of azide compounds is less convenient due to the well known explosiveness of azidic structures.

Amlodipine prepared according to the processes described in the reported literature is finally isolated, purified and converted to its acid addition salts if desired.

DESCRIPTION OF THE SOLUTION TO THE TECHNICAL PROBLEM WITH EXAMPLES OF EMBODIMENT

It is the aim of the present invention to prepare amlodipine benzenesulphonate in a simple and easily feasible way, which would afford the desired substance in high overall yield and high purity without any need for a previous preparation and isolation of amlodipine in its free base form and isolation of its precursor from the crude reaction mixture obtained by Hantzsch's synthesis.

This aim is achieved by first using Hantzsch's synthesis of unsymmetrical 1,4 dihydropyridine diesters by condensing ethyl 4-[2-(N-tritylamino)ethoxy]acetoacetate, methyl-(E)-3-amino crotonate and 2-chlorobenzaldehyde in a methanolic medium at the reflux temperature of the reaction mixture to prepare 3-ethyl 5-methyl (±) 2-[2-(N-tritylamino)-ethoxymethyl]-4-(2-chlorophenyl)-1,4-dihydro-6-methyl-3,5-pyridinedicarboxylate, which is a new compound not described in the literature and a precursor of amlodipine, whose amino group is protected by a trityl group. The process of the invention is based on the simultaneous splitting-off of the protective trityl group from the obtained precursor of amlodipine, which in the process is not isolated from the crude reaction mixture. which is at once reacted with benzenesulphonic acid, and on the direct isolation of amlodipine benzenesulphonate without any formation of amlodipine in the form of its base at all. The reaction takes place in the temperature range between 20° C. and reflux temperature. However, in order to remove the split-off triphenylmethyl methyl ether (possibly accompanied by some triphenylmethanol) from the reaction mixture. stirring at a temperature below 0° C., preferably at about −10° C., is necessary.

From the crude reaction mixture, which is in the form of a resin, amlodipine benzenesulphonate can be isolated by means of a continuous extractor for extraction with a solvent having a lower specific density. In this way polar and non-polar admixtures are removed from the three-phase system resin-water-organic solvent, which is followed by the digestion of the desired compound in an appropriate organic solvent such as ethyl acetate, at reduced temperature (about 0° C.), to remove the admixtures and to render possible the separation of crystals of amlodipine benzenesulphonate, which, in order to obtain its high purity, is finally further purified by recrystallization from an appropriate organic solvent, such as methanol, followed by digestion in the same solvent at a lower temperature (about 0° C.).

The novelty and improvement of the present invention resides in the simultaneous splitting-off of the protecting trityl group from the precursor of amlodipine and the direct isolation of amlodipine benzenesulphonate without the necessity of an intermediary preparation and isolation of amlodipine in its free base form and reaction of this base to the benzenesulphonate salt, as described in the processes known from the literature. The benzenesulphonic acid acts at the same time as a means of splitting-off the protective trityl group from the precursor of amlodipine as well as a means of the direct preparation of the desired salt.

In the process of the invention it is neither necessary to isolate the precursor of amlodipine from the crude reaction mixture. Instead, benzenesulphonic acid can be added to the obtained crude methanolic reaction mixture and after the completion of the reaction, the title compound can be isolated. By the process of the present invention one step of the reaction is spared, the desired compound is obtained in good yield and reductions, which are sometimes quite exacting, are avoided. 2-Chlorobenzaldehyde and methyl(E)-3-aminocrotonate, which are necessary for Hantzsch's synthesis of asymmetric 1,4-dihydropyridine diesters, are commercially available, whereas ethyl-4-[2-(N-tritylamino)ethoxy]-acetoacetate is prepared in the way as exemplified in Example 3 or 4. N-trityl-2-aminoethanol, which is needed for the preparation of this acetoacetate, can be prepared in the way, which is described by P. F. Buckus, P. J. Saboniene and D. B. Lemetiene, Zh. Obsch. Khim. 6, 1984 (1970), but preferably by an improved method exemplified in Example 1 or 2, where the reaction is not carried out in the malodorous pyridine and at reflux temperature but in an isopropanolic medium and at room temperature, thereby achieving a higher yield of the reaction and a higher content of the desired N-trityl-2-aminoethanol, which represents a further enrichment of the techniques.

The overall course of the reaction is shown in Scheme 1.

The invention is illustrated but in no way limited by the following Examples:

PREPARATION OF STARTING MATERIALS

EXAMPLE 1

N-trityl-2-aminoethanol

A mixture of isopropanol (750 ml), diethylamine (75 ml), ethanolamine (98%, 62.3 g, 1 mole) and triphenylchloromethane (97%, 143.7 g, 0.50 moles) was stirred at room temperature for 3 hours. The resulting solution was then poured into ice-cold water (4 l) under continuous stirring and the resulting precipitate was filtered off and dried. The crude product was digested in toluene (340 ml), then filtered off and dried in vacuo at 60° C. Thus 130 g (85%) of the pure desired compound were obtained.

EXAMPLE 2

N-trityl-2-aminoethanol

A mixture of ethanolamine (2-aminoethanol) (98%, 1.750 kg, 28.0 moles) in isopropanol (7.0 l) was stirred to yield a homogeneous solution. Thereto triphenylchloromethane (97%, 2.020 kg, 7.03 moles) was added slowly within 1 h at room temperature with stirring, whereat the temperature was not to exceed 30° C. After completed dissolution of triphenylchloromethane (whereat ethanolamine hydrochloride separated as a white precipitate) the reaction mixture was stirred for another hour and cooled to room temperature. The precipitate, which separated, was filtered off and the filtrate was poured into ice-cold water (8.0 l). The precipitate, which separated, was filtered off and dried in vacuo at a temperature not exceeding 50° C. Thus there were obtained 2.120 kg (98%) of the desired compound.

EXAMPLE 3

Ethyl-4-[2-(N-tritylamino)ethoxy]acetoacetate

Sodium hydride (60%, 45.7 g, 1.14 moles) in liquid paraffin and anhydrous tetrahydrofuran (300 ml) were introduced into a reactor, which was then blown through with nitrogen. Pure N-trityl-2-aminoethanol (100% pure, 130 g, 0.42 moles) dissolved in tetrahydrofuran (380 ml) was then added dropwise within 1 hour at room temperature with stirring and blowing nitrogen through the reactor, whereat the temperature was not to exceed 40° C. After the completion of the dropwise addition, the reaction mixture was stirred for another hour at room temperature and then cooled to 0° C. To the reaction mixture a solution of ethyl-4-chloroacetoacetate (98%, 70.9 g, 0.42 moles) in anhydrous tetrahydrofuran (80 ml) was added within 1 hour with stirring, blowing nitrogen through the reactor and cooling in such a way that the temperature did not exceed 20° C. After the completion of the addition of the reactant, the reaction mixture was stirred at room temperature for additional 20 hours. Ethanol (55 ml) was then added to the reaction mixture and the resulting mixture was diluted with water (550 ml) and neutralized with hydrochloric acid (about 60 ml) to a pH value of 7. The organic phase was separated and evaporated in vacuo, the obtained crude product was dissolved in methanol (500 ml) and liquid paraffin, which separated, was removed. The remaining solution was transferred to a rotary vacuum evaporator and water (170 ml) was added thereto at high rotation speed to obtain a homogenous emulsion, from which water and methanol were evaporated, to obtain 160.5 g (85 %) of a product containing 96 % of the title compound [assessed by the HPLC (high performance liquid chromatography) method], which could be used in the next reaction step without any further purification. If desired, the pure title compound could be prepared by chromatographic purification on silica gel (eluent: diethyl ether:n-pentane 1:1 (v/v)).

Analysis: NMR (TMS, CDCl$_3$, 60 Hz): δ: 1.20 (t, 3H, J=7 Hz); 2.37 (t, 2H, J=5.5 Hz); 3.47 (s, 2H); 3.57 (t, 2H, J=5.5 Hz); 4.00 (s, 2H); 4.10 (q, 2H, J=7 Hz); 7.1–7.6 (m, 15H).

EXAMPLE 4

Ethyl 4-[2-(N-tritylamino)ethoxy]-acetoacetate

Sodium hydride (60%, 0.680 kg, 17.0 moles) in liquid paraffin and anhydrous tetrahydrofuran (3.20 l) were introduced into a reactor, which was then blown through with nitrogen. N-trityl-2-aminoethanol (2.120 kg, 6.94 moles) (obtained in Example 2) dissolved in anhydrous tetrahydrofuran (5.45 l) was then added at room temperature with stirring and blowing nitrogen through the reactor, whereat the temperature was not to exceed 30° C. After completed addition the reaction mixture was stirred for another half an hour at room temperature and then cooled to a temperature of between −5° C. and −10° C. To the reaction mixture a solution of ethyl-4-chloroacetoacetate (98%, 1.160 kg, 6.90 moles) in anhydrous tetrahydrofuran (1.35 l) was added with stirring, blowing nitrogen through the reactor and cooling. After completed addition of the reactant, the reaction mixture was stirred for 5 hours, whereat the temperature was not to exceed +5° C., and then stirred at room temperature for additional 15 hours. Absolute ethanol (0.5 l) was then added with blowing nitrogen through the reactor and intensive stirring. The blowing through of nitrogen and stirring were then stopped and the reaction mixture was diluted with water (30 l) and the liquid paraffin, which separated, was removed. The obtained solution was then neutralized with hydrochloric acid (0.8 kg of concentrated acid) to a pH value of 7. The organic phase was separated and concentrated in a rotary vacuum evaporator first at a temperature of 40° C. The temperature was gradually raised to 70° C. to obtain 2.520 kg (75%) of a product containing 87.5% of the title compound [assessed by the HPLC (high performance liquid chromatography)method], which was used in the next reaction step without any further purification.

PROCESS OF THE INVENTION

EXAMPLE 5

3-ethyl 5-methyl (±) 2-[(2-aminoethoxy)-methyl]-4-(2-chlorophenyl)-1,4-dihydro-6-methyl-3,5-pyridinedicarboxylate monobenzene sulphonate 2-chlorobenzaldehyde (95%, 50.2 g, 0.35 moles), methyl(E)-3-aminocrotonate (97%, 41.5 g, 0.35 moles) and ethyl-4-[2-(N-tritylamino)ethoxy]acetoacetate (160.5 g, 0.35 moles, content 96%, obtained in Example 3) were dissolved in methanol (350 ml). The reaction mixture was heated at reflux temperature for 10 hours and then cooled to about room temperature. To the crude mixture of the obtained 3-ethyl 5-methyl (±) 2-[2-(N-tritylamino)-ethoxymethyl]-4-(2-chlorophenyl)-1,4-dihydro-6-methyl-3,5-pyridine dicarboxylate an aqueous solution of benzenesulphonic acid (105 g, 0.53 moles, 80%) was added. The reaction mixture was reheated for 3 hours at reflux temperature, then cooled to −10° C. and stirred at this temperature for 10 hours. The precipitate, which separated, was filtered off. The filtrate was concentrated in vacuo to obtain a viscous resin. While still warm, this resin was transferred to a 2 l continuous extractor for extraction with a solvent having a lower specific density,. Hot water (1500 ml) and toluene (1500 ml) were added to the resin and into the distillate receiver respectively and non-polar impurities were continuously extracted for 24 hours from the three-phase system resin-water-toluene (the resin is neither soluble in water nor in toluene). The oil, which was formed from the resin, was separated from water and toluene and dissolved in chloroform (1500 ml). The chloroform solution was again transferred to the 2 l continuous extractor for the extraction with solvents having a lower specific density and water (1500 ml) was given into the distillate receiver. For 24 hours polar impurities were continuously extracted with water, the chloroform layer was separated and the solvent was evaporated in vacuo. Thus, a brown foam (37.2 g) was obtained, which solidified to an amorphous solid, to which ethyl acetate (90 ml) was added and the obtained mixture was stirred for 1 hour at 0° C. Thereat crystals of crude amlodipine benzenesulphonate were formed from the amorphous material, which were filtered off and dried in vacuo at 60° C. The dried crude product (24.1 g) was recrystallized from methanol (50 ml). The still wet product was digested for 2 hours at 0° C. in methanol (25 ml), then it was filtered off and dried in vacuo at 60° C. Thus, 13.8 g of white crystals of amlodipine benzenesulphonate of high purity (over 99% purity as assessed by HPLC method), m.p. 201.0° C., were obtained.

EXAMPLE 6

3-ethyl 5-methyl (±) 2-[(2-aminoethoxy)-methyl]-4-(2-chlorophenyl)-1,4-dihydro-6-methyl-3,5-pyridinedicarboxylate monobenzenesulphonate Ethyl-4-[(2(N-tritylamino)ethoxy)]acetoacetate (2.520 kg, 5.12 moles, content 87.5%) (obtained in Example 4), methyl(E)-3-aminocrotonate (97%, 0.608 kg, 5.12 moles) and 2-chlorobenzaldehyde (98%, 0.734 kg, 5.12 moles) were dissolved in methanol (6.40 l), the reaction mixture was heated at reflux temperature for 15 hours and then cooled to about room temperature. To the cooled crude solution of the obtained 3-ethyl 5-methyl (±)2-[2-(N-tritylamino)-ethoxymethyl]-4-(2-chlorophenyl)-1,4-dihydro-6-methyl-3,5-pyridine dicarboxylate in methanol, a solution of technical grade benzenesulphonic acid (0.980 kg, 92%) in methanol (1.95 l) was slowly added with stirring. The reaction mixture was reheated for 3 hours at reflux temperature with stirring, slowly cooled to a temperature about 0° C. and stirred at this temperature for additional 5 hours. The precipitate of triphenylmethyl methylether, which separated thereat, was filtered off. The filtrate was concentrated in vacuo, first at a temperature of 40° C., which was gradually raised to 70° C., whereat a brown viscous resin was obtained. This resin was transferred together with water (4.2 l) into a continuous extractor for extraction with a solvent having a lower specific density, and non-polar impurities were continuously extracted for 48 hours with a mixture of toluene (1.38 l) and n-heptane (1:1 v/v). The contents of the reactor were transferred to a separatory funnel as were the residues in the reactor, which were dissolved in chloroform (0.47 l) and added into the separatory funnel. The oil which formed from the resin was separated from both the aqueous and the organic phases, and then evaporated in the rotary vacuum evaporator to yield an amorphous solid, to which ethyl acetate (0.75 l) was added with stirring at a temperature of 0° C. Thereat the amorphous solid was transformed to the crystalline crude amlodipine benzenesulphonate. The crystals were filtered off and dried in vacuo at 70° C. The dried product (0.640 kg) was crystallized from methanol (1.15 l) and the still wet product was digested for 1 hour at 0° C. in methanol (0.290 l), then filtered off and dried in vacuo at a temperature not exceeding 70° C. Thus there were obtained 0.300 kg of crystals of high purity amlodipine benzenesulphonate (content over 98%). The product was recrystallized with methanol (0.540 l) and the still wet product was digested in methanol (0.200 l) for 1 hour at 0° C. and then filtered off and dried in vacuo at a temperature not exceeding 70° C. Thus, 0.200 kg of white crystals of amlodipine benzenesulphonate of high purity (over 99% purity as assessed by HPLC method), m.p. 201.0° C., were obtained.

REFERENCE EXAMPLE

For the characterization of the precursor of amlodipine benzenesulphonate of Example 5, crude 3-ethyl 5-methyl (±) 2-[2-(N-tritylamino)-ethoxymethyl]-4-(2-chlorophenyl)-1,4-dihydro-6-methyl-3,5-pyridinedicarboxylate was purified by column chromatography on silica gel (eluent: diethyl ether:petroleum ether 1:3 (v/v)). The purified product was obtained in the form of a yellow foam having the following spectrum:

NMR (CDCl₃,TMS, 60 Hz): δ: 1.19 (t, 3H, J=7 Hz); 1.45 (s, 3H); 2.46 (t₂, 2H, J=5 Hz); 3.64 (s, 2H); 3.7 (t, unclear 2H); 4.10 (q, 2H, J=7 Hz); 4.75 (s, 2H); 5.50 (s, 1H); 7.0-7.8 (m, 19H).

SCHEME 1
PREPARATION OF STARTING MATERIALS

Step 1

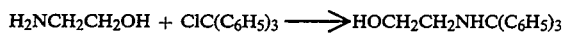

Step 2

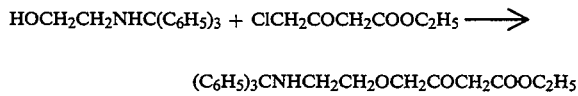

PROCESS OF THE INVENTION

Step 3

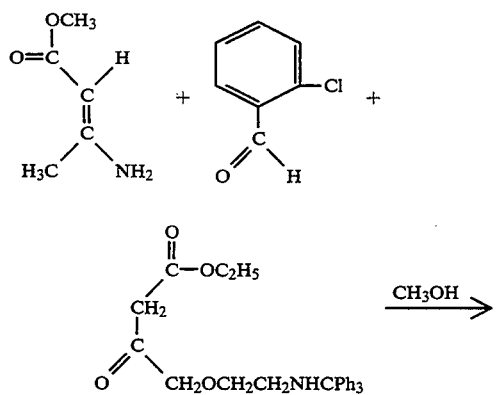

-continued
SCHEME 1

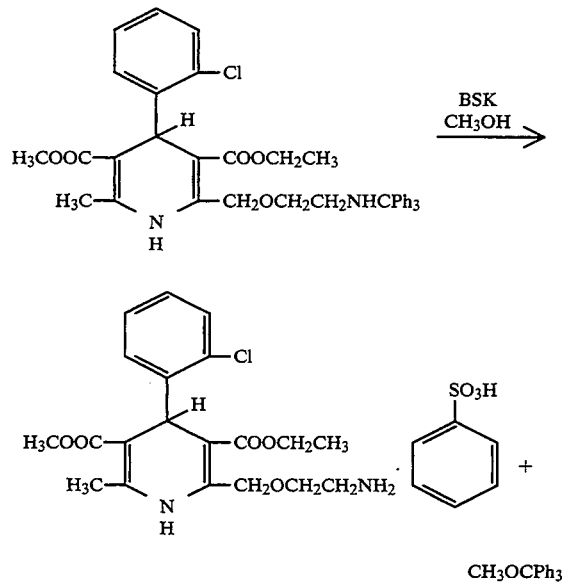

BSK = benzenesulphonic acid
Ph = phenyl

We claim:
1. A process for the preparation of 3-ethyl 5-methyl (±) 2-[(2-aminoethoxy)methyl]-4-(2-chlorophenyl)-1,4-dihydro-6-methyl-3,5-pyridinedicarboxylate monobenzenesulphonate (amlodipine benzencsulphonate) of formula

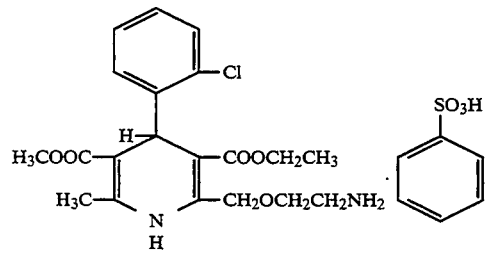

characterized in that 3-ethyl 5-methyl (±) 2-[2-(N-tritylamino)-ethoxymethyl]-4-(2-chlorophenyl)-1,4-dihydro-6-methyl-3,5-pyridinedicarboxylate is reacted with benzenesulphonic acid in a methanolic or an aqueous methanolic medium at a temperature from 20° C. to the reflux temperature.

2. The process of claim 1 wherein the title compound is isolated and purified including stirring after completion of the reaction at a temperature below 0° C. to remove tiphenylmethyl methyl ether.

3. The process of claim 2 wherein said temperature is about −10° C.

4. The process of claim 3 wherein reacting with benzenesulphonic acid is carried out at reflux temperature.

5. The process of claim 1 wherein reacting with benzenesulphonic acid is carried out at reflux temperature.

* * * * *